United States Patent [19]

Doty et al.

[11] Patent Number: 4,836,012
[45] Date of Patent: Jun. 6, 1989

[54] GAS SENSOR

[75] Inventors: Mitchell E. Doty, Chalfont; Ferenc J. Schmidt, Bryn Mawr, both of Pa.

[73] Assignee: Ametek, Inc., Harleysville, Pa.

[21] Appl. No.: 199,123

[22] Filed: May 26, 1988

[51] Int. Cl.$^4$ .............................................. G01N 27/00
[52] U.S. Cl. ..................... 73/23; 136/255; 136/291; 357/15; 357/30; 324/71.5; 338/34
[58] Field of Search ............... 136/255, 291; 357/15, 357/30 C; 73/23; 338/34; 324/71.5

[56] References Cited

U.S. PATENT DOCUMENTS

| | | | |
|---|---|---|---|
| 3,793,605 | 2/1974 | Fehlner | 338/34 |
| 3,927,977 | 12/1975 | Jacobs | 422/86 |
| 4,030,340 | 6/1977 | Chang | 73/23 |
| 4,035,197 | 7/1977 | Raychaudhuri | 136/255 |
| 4,058,368 | 11/1977 | Svensson et al. | 422/88 |
| 4,103,227 | 7/1978 | Zemel | 324/65 R |
| 4,302,530 | 11/1981 | Zemel | 437/229 |
| 4,313,338 | 2/1982 | Abe et al. | 73/23 |
| 4,345,107 | 8/1982 | Fulop et al. | 136/255 |
| 4,453,151 | 6/1984 | Leary et al. | 338/34 |
| 4,481,499 | 11/1984 | Arima et al. | 338/34 |
| 4,495,375 | 1/1985 | Rickus et al. | 136/255 |
| 4,615,772 | 10/1986 | Hetrick | 204/1 T |

FOREIGN PATENT DOCUMENTS 56-70448  6/1981  Japan ........................................ 73/23

OTHER PUBLICATIONS

D. E. Carlson et al., *Proceedings, 2nd E.C. Photovoltaic Solar Energy Conference* (1979), pp. 312–319.
I. M. Dharmadasa et al., *Electronics Letters*, vol. 16, pp. 201–202, (1980).
Kirk–Othmer, *Encyclopedia of Chemical Technology*, vol. 6, pp. 179–189 (for a discussion of clathrates).
ACS Symposium Series (1986), "*Fundamentals and Applications of Chemical Sensors*", edited by D. Schuetzle, et al., Chapter 9, pp. 155–165 (for a discussion of PC), and Chapter 11, pp. 178–202 (for a discussion of solid state gas sensors generally).

*Primary Examiner*—Aaron Weisstuch
*Attorney, Agent, or Firm*—Amster, Rothstein & Ebenstein

[57] ABSTRACT

A gas sensor comprises a photovoltaic cell which, upon exposure to light, develops a photovoltage or photocurrent which varies as a function of the type of gas sorbed. The cell includes in order a conductor, an N-type light-absorbing semiconductor, and a thin light-transmitting gas-absorbing metal Schottky layer having electrical properties which vary with the type of gas sorbed therein.

64 Claims, 2 Drawing Sheets

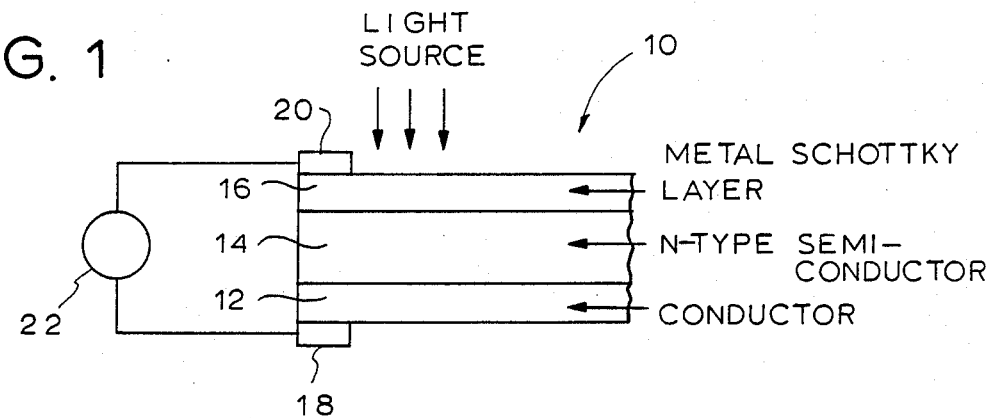
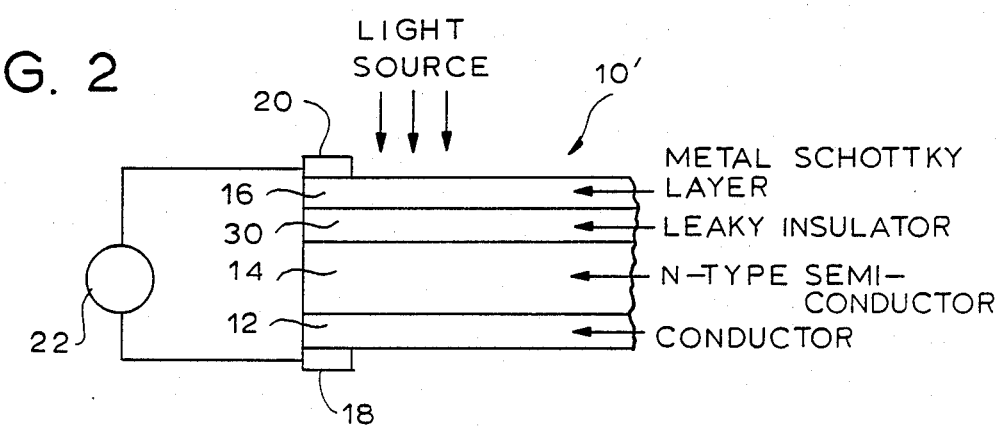
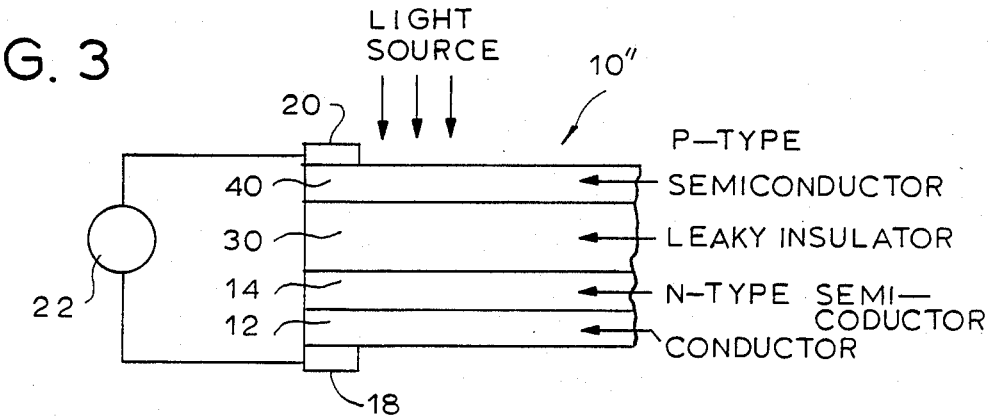

GAS SENSOR

BACKGROUND OF THE INVENTION

The present invention relates to a gas sensing device, and more particularly concerns a gas sensing device whose electrical properties vary with the type of gas sorbed therein.

The literature contains descriptions of many types of devices and methods which are capable of detecting gases including chemical reactions which give color changes or pH changes, instrumental methods including mass spectrometers and infrared analyzers, electrochemical techniques which utilize the properties of dissolved gases, solid state devices which detect changes in thermal and electrical conductivities of different gases, thin film solid state devices such as thin oxide films, organic semiconductor films which exhibit electrical conductivity changes as a function of ambient gas composition, and chemical field effect transistors.

A wide variety of different means have been used to detect the presence of particular gases over time, these means ranging from the organic (such as the use of a canary in a coal mine) to the complex semiconductor or solid state devices described in the ACS Symposium Serie 309 "Fundamentals and Applications of Chemical Sensors" (1986 American Chemical Society) and in patents such as U.S. Pat. No. 4,058,368 (disclosing a hydrogen detector MIS device comprising a semiconductor substrate, a metal electrode of palladium, nickel, platinum or palladium alloy, and an intervening insulator situated between the semiconductor substrate and the metal electrode). Devices of silicon and palladium Schottky layer have been used as gas detectors, the dark current or capacitance being measured by impressing an external voltage across the diode, In one important aspect the earlier organic gas sensor—namely, the canary—provided an advantage not found in the more sophisticated devices presently in favor. The canary did not require an outside power supply. By way of contrast, the prior art gas sensing devices have been subjected to external power or internal power supply (e.g., battery) failures which could lead to deactivation of the device even in situations where a momentary deactivation could be fatal. In those applications where the cost is warranted, fail safe devices are utilized to bring the user's attention the failure of the power supply, but the device remains inoperative for its intended purpose of detecting gas.

Accordingly, it is an object of the present invention to provide a self-powered gas detecting device which requires neither an internal electrical storage system nor connection to an external power supply.

Another object is to provide such a gas sensing device which, when exposed to light, generates its own photovoltage or photocurrent, such photovoltage or photocurrent changing as a function of the ambient gas composition.

Still another object is to provide such a device which can discriminate between particular gases.

A further object is to provide such device which is inexpensive to construct and maintain and easy and economical to operate.

SUMMARY OF THE INVENTION

It has now been found that the above and related objects of the present invention are attained in a gas sensing device comprising a photovoltaic cell which, upon exposure to light, develops a photovoltage or photocurrent which varies as a function of the type of gas sorbed. In a first embodiment the cell includes in order a conductor, an N-type light-absorbing semiconductor, and a light-transmitting gas-absorbing metal Schottky layer having electrical properties which vary with the type of gas sorbed therein.

Preferably the metal Schottky layer is non-$H_2$-absorbent and composed of a metal selected from the group consisting of palladium and nickel. The N-type light-absorbing semiconductor is CdTe or a material selected from the group consisting of Si, $CuInSe_2$, CdSe, $Cd_{(1-x)}Hg_xTe$, and GaAs, preferably Si or CdTe. The electrical properties may also vary with the quantity of the gas sorbed up to a saturation point.

The electrical properties include leakage current, capacitance, resistance and the cell parameters of open circuit voltage and short circuit current.

In a second embodiment the device additionally includes, intermediate the semiconductor and the metal Schottky layer, a light-transmitting gas-absorbing insulating layer of a dielectric having electrical properties which vary with the type of gas sorbed therein. The dielectric is selected from the group consisting of phthalocyanine and clathrating compounds. The phthalocyanine may be metal-substituted, preferably with iron or zinc. The clathrating agent is a solid, preferably thiourea, and the guest compound is a gas. The metal Schottky layer is preferablly gold.

In a third embodiment, a thin P-type light-transmitting, gas-penetrable semiconductor replaces the metal Schottky layer of the second embodiment.

BRIEF DESCRIPTION OF THE DRAWING

The above brief description, as well as further objects and features of the present invention, will be more fully understood by reference to the following detailed description of the presently preferred, albeit illustrative, embodiments of the present invention when taken in conjunction with the accompanying drawing wherein:

FIG. 1 is a schematic view of a first embodiment of a gas sensor according to the present invention;

FIG. 2 is a schematic cross-section view of a second embodiment of gas sensor according to the present invention; and FIG. 3 is a schematic view of a cross-section of a third embodiment of a gas sensor according to the present invention.

DETAILED DESCRIPTION OF THE PREFERRED EMBODIMENTS

Figure 4:
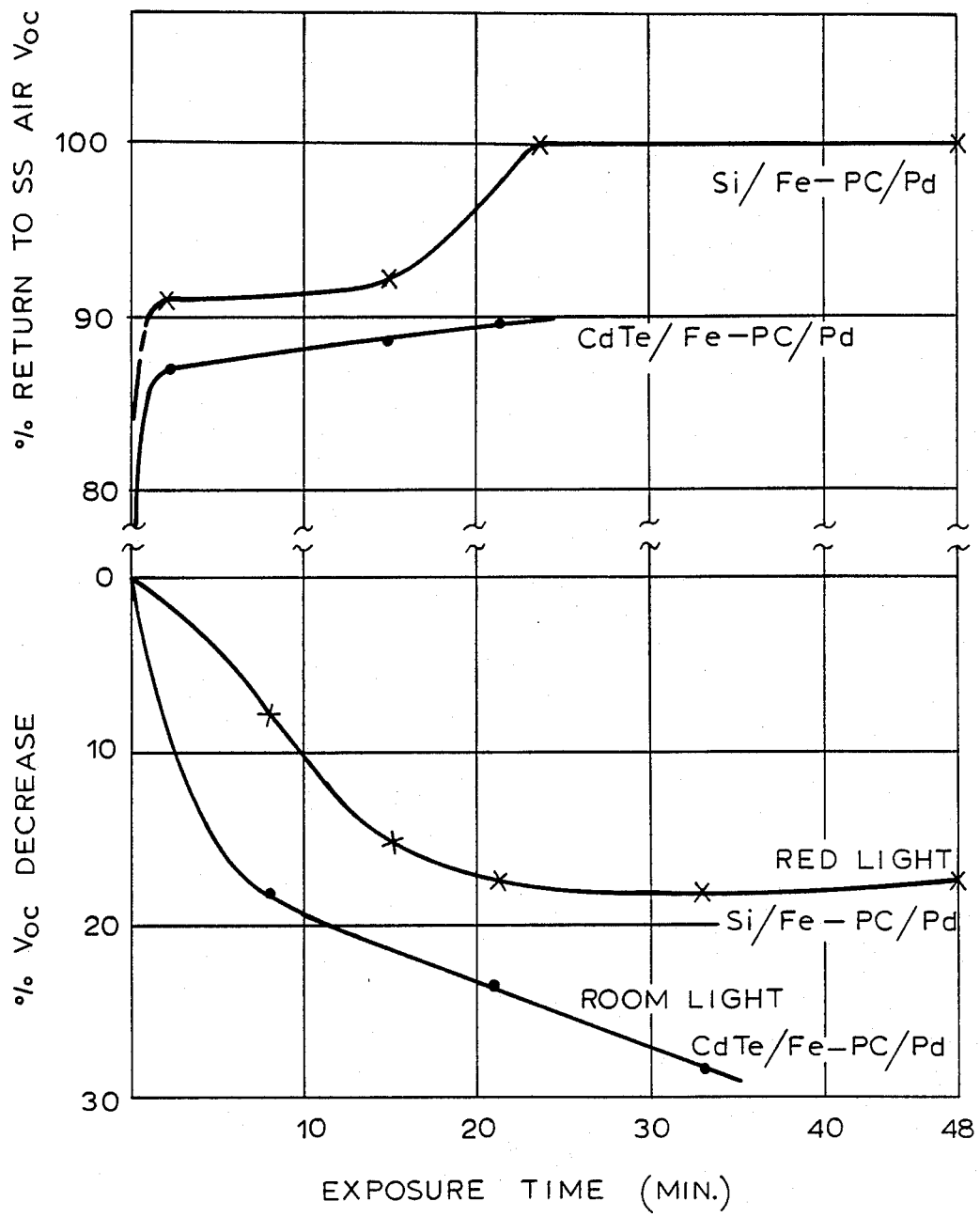
FIG. 4 is a graphical plot of % $V_{oc}$ decrease vs. time and % return to steady state air $V_{oc}$ vs time for exemplary devices of the invention.

Referring now to the drawing, and in particular to FIG. 1 thereof, therein illustrated is a gas sensing device according to the present invention, generally designated by the reference numeral 10. The gas sensor 10 comprises a photovoltaic cell which, upon exposure to light, develops a photovoltage or photocurrent which varies as a function of the type of gas sorbed. It includes in order a conductor 12, an N-type light-absorbing semiconductor 14, and a thin light-transmitting gas-absorbing metal Schottky layer 16 having an electrical property which varies with the type of gas sorbed therein. First and second conductive elements 18, 20 are in electrical communication at one end with the conductor 12 and metal Schottky layer 16, respectively, and at the other end with a measuring circuit 22 which responds to the photovoltage or photocurrent developed by the cell upon exposure to light and which varies as a function of the type of gas sorbed. It will be appreciated that this embodiment of the present invention requires no power source for operation of the gas sensing device other than the light.

The conductor 12 may be formed from any of the materials customarily employed as conductors in the semiconductor art and will preferably be a metal selected for its suitability as a substrate, e.g., Ni-coated steel.

The N-type semiconductor 14 may be any N-type light-absorbing semiconductor such as CdTe, Si, CuInSe$_2$, CdSe, Cd$_{1-x}$(Hg)$_x$Te, and GaAs, CdTe and Si being preferred. The N-type semiconductor is formed in conventional fashion. For example, cadmium telluride (CdTe) is electrodeposited on the metal substrate 12, and the electrodeposited cadmium telluride is then heat treated at 300°–310° C. in an inert atmosphere (a nitrogen atmosphere being preferred) with oxygen being excluded. Silicon may be formed by the Czocharlski process of pulling monocrystalline silicon from a melt. The thickness of the N-type semiconductor layer is not critical, and may conveniently be one micron.

The metal Schottky layer 16 is a very thin metal layer which acts as a light transmitting Schottky barrier to the N-type semiconductor and is presumably of a "fish net" or other discontinuous nature such that it is pervious or permeable to gas molecules of the type to be detected. The thickness of the metal Schottky layer 16 is preferably 100–200 angstroms, although thinner and thicker layers which do not adversely affect the function of the metal Schottky layer may also be employed. Thus, the metal Schottky layer must be thin enough to permit light transmission and gas permeability to the gas molecules to be detected. For the detection of hydrogen, liquid petroleum gas (L.P.G.) and acetylene, a hydrogen absorbing metal is required; thus, palladium and nickel are suitable, while gold is not. Preferably the metal Schottky layer is selected from the group consisting of the platinum group metals (e.g., Ni, Pd, Pt), the hydrogen storage metal alloys (e.g., alloys of Ti, Fe, Ni such as TiNi, MnFeNi, MgNi, etc.), the rare earth elements, titanium, tungsten, zirconium, and tantalum. Palladium and nickel are especially preferred, and these materials may alo be useful in detecting labile hydrides such as silanes, arsine, stibine, etc.

The metal Schottky layer 16 is applied to the exposed surface of the N-type semiconductor 14 in a vacuum deposition system from a heated substrate. While the simple diode embodiment 10 of the present invention exhibits a high sensitivity to such gases as hydrogen, liquid petroleum gas, and acetylene, it exhibits little, if any, sensitivity to other gases devoid of labile hydrides.

The conductor members 18, 20 may be any of the conducting elements typically used as connectors in the electrical arts, and may conveniently be leads of copper wire. The measuring device 22 may be any device which reacts and responds to a varying photovoltage or photocurrent—for example, a voltmeter or ammeter. For particular applications—for example, where the gas sensing device is to attract attention or signal danger—the measuring device may produce a sound or light which varies with the photovoltage or photocurrent or may have a limit or cutoff mechanism such that the photovoltage or photocurrent must cross a certain threshhold (and be either higher or lower than the threshhold value) before the visual or aural indicators are activated. Especially where the measuring device 22 has an attention-attracting aspect, it may be used to control operation of a slave attention-attracting mechanism having an independent power supply (whether self-contained or external).

The electrical properties of the metal Schottky layer which varies with the type of gas sorbed therein may be, for example, capacitance, resistance, and the circuit parameters of open circuit voltage and short circuit current. Other electrical properties may also be used. For the first embodiment it has been found that the open circuit voltage (Voc) in particular varies greatly with the type of gases sorbed. It will be appreciated that for particular metal Schottky layers and particular gases, the electrical properties may vary not only with the type of gases sorbed, but also the quantity of the gas sorbed up to a saturation point.

Referring now to FIG. 2, therein illustrated is a second embodiment of the present invention, generally designated 10'. The second embodiment 10' is basically similar in many respects to the first embodiment 10 and includes a conductor 12, an N-type semiconductor 14, a metal Schottky layer 16, leads 18, 20 and a measuring circuit 22. However, in the second embodiment 10' a leaky insulator layer 30 is sandwiched between the N-type semiconductor 14 and metal Schottky layer 16 in order to provide a device which offers sensitivity to a larger variety of gases as well as the opportunity to create a device affording greater selectivity as to the gases to which it responds. The enhanced discrimination or selectivity between different gases is possible because the metal Schottky layer 16 can serve as a fixed or invariant barrier material for the N-type semiconductor 14 with the insulator 30 being varied independently to act as the selectively pervious or permeable barrier. Accordingly, the use of a non-hydrogen absorbing metal Schottky layer 16, such as gold, may be useful.

The metal Schottky/insulator/N-type semiconductor conductor embodiment 10' may be designed to provide sensitivity to aliphatic hydrocarbons, ammonia, carbon monoxide, alcohols, ketones, and water vapor which are not sensed by the simple metal Schottky/N-type semiconductor/conductor diode embodiment 10. In addition, the insulator-modified diode may be sensitive to the same gases (e.g., hydrogen, liquid petroleum gas, acetylene, etc.) which the unmodified diode detects. It is a matter of mere routine experimentation to determine the identity of the particular insulator layers 30 to enable a device to be made sensitive to particular gases. Indeed, a gas sensor may be constructed for the simultaneous detection of multicomponent gases through the integration of several smaller devices (whether of the first or second embodiment types) into a larger device.

The leaky insulator or gas-absorbing dielectric layer 30 is preferably a thin layer (about 200–1500 angstroms) of any organic or inorganic insulating or dielectric material which sorbs the gas to be detected and which, in so doing, changes the dielectric property of the material. For example, the sorbing of the gas to be detected may change the capacitance, resistance, open circuit voltage or short circuit current. Typically the sorbing of the gas changes the leakage current, thereby reducing the short circuit current. The light-transmitting gas-absorbing leaky dielectric or insulation layer 30 is preferably selected from the group consisting of phthalocyanines (hereinafter PC) and clathrating compounds.

Such materials are discussed in Kirk-Othmer, *Encyclopedia of Chemical Technology*, Vol. 6, pp. 179–189 (for a discussion of clathrates) and the ACS Symposium Series 309 (1986), "Fundamentals and Applications of Chemical Sensors", edited by D. Schuetzle, et al., Chapter 9, pp. 155–165 (for a discussion of PC), and Chapter 11, pp. 178–202 (for a discussion of solid state gas sensors generally). The leaky insulator layer 30 should be thick enough to avoid breaks or holes therein.

The PC may be used in its unsubstituted or $H_2$ form or in one of its metal-substituted forms, such as the iron- or zinc-substituted forms (Fe-PC or Zn-PC). The various forms provide sensitivity to different gases, as indicated in Table I.

A clathrate is a substance which fixes gas or liquids as inclusion complexes so that the complex may be handled in solid form and the included constituent subsequently released. For the purposes of the present invention, the "host" clathrating compound must be a solid able to complex a gaseous "guest" compound. A large number of clathrating compounds and their selectivity are so well known that the selection of particular clathrating compounds for particular gas sensitivities may be simply a matter of literature research or at most routine experimentation. A preferred clathrating agent is thiourea.

Referring now to Table I, therein illustrated are the sensitivities of devices according to the first embodiment (without PC) and the second embodiment (with free PC, iron-substituted PC and zinc-substituted PC) for liquid petroleum gas, dilute hydrogen, ammonia and dilute carbon monoxide. The results are expressed as the percentage decrease is open circuit voltage (Voc) upon exposure to the gas as a function of the time exposed. (In certain instances this decrease may actually be an increase in open circuit voltage). The measuring circuit 22 was a voltmeter. The device was exposed to very dim room light through the metal Schottky layer.

The first and second embodiments of the present invention illustrate great sensitivity to a wide variety of gases which require monitoring of their concentrations in work places as, above certain concentration limits, they represent explosive, fine or health hazards. While the sorbing of most gases reduces the open circuit voltage, in certain instances the sorbing of particular gases may result in a significant increase in the open circuit voltage (for example, the sorbing of carbon monoxide by a device of the second embodiment utilizing a zinc-substituted PC.)

Referring now to FIG. 3, therein illustrated is a third embodiment of the present invention generally designated 10''. The third embodiment 10'' is basically similar in many respects to the second embodiment 10' and includes a conductor 12, an N-type semiconductor 14, a leaky insulator 30, leads 18, 20, and a measuring circuit 22. However, in the third embodiment 10'', a P-type semiconductor 40 replaces the metal Schottky layer 16 of the second embodiment. The P-type semiconductor 40 forms a light-transmitting layer which is permeable or pervious to the type of gas to be sorbed. Like the second embodiment, the third embodiment provides sensitivity to a larger variety of gases and enhanced discrimination or selectivity between different gases. The P-type semiconductor 40 is preferably a thin, discontinuous, vacuum deposited layer of P-type CdTe, P-type $CuInSe_2$, P-type Si, etc. and may be 100 to 200 angstroms in thickness to allow for gas penetration, although the layer structure is more important than its thickness.

If for a particular application it is unnecessary that a device according to the second or third embodiments be self-powering (that is, the device need not have a photovoltage or photocurrent), the light-transmitting properties of the metal Schottky layer 16, the leaky insulator 30, and the P-type semiconductor 40 are unnecessary and the changes in the electrical properties may be measured by other conventional means, such as standard electrical bridge circuits for the measurement of current, resistance or capacitance.

EXAMPLES

Unless otherwise noted, all tests were performed at 60° C.

EXAMPLE I

Silicon and cadmium telluride devices according to the second embodiment were fabricated as follows: a 1 $cm^2$ N-type wafer of Si or CdTe was coated with 200 angstroms of iron-substituted phthalocyanine (Fe-PC), followed by 100 angstroms of a palladium Schottky metal. Leads were attached to the top and bottom and connected to a voltmeter.

The silicon device (Si/Fe-PC/Pd) was continuously exposed to a weak red light, and the cadmium telluride device (CdTe/Fe-PC/Pd) was continuously exposed to room light. Both devices were then exposed to dry air until they reached a steady state open circuit voltage (Voc) value. Then each device, still under light exposure, was exposed to liquid petroleum gas (L.P.G.), and the percentage decrease in the open circuit voltage from the steady state dry air Voc was recorded as a function of the exposure time. The results were recorded in FIG. 4 and indicate that the CdTe device showed greater sensitivity to L.P.G. (that is, a greater percentage change in Voc) than the Si device.

The L.P.G. was then flushed out of the system and replaced by dry air. The percentage return to the steady state dry air Voc (that is, the present Voc as a percentage of the original Voc under dry air) was recorded as a function of the time of exposure to the dry air. The results were recorded in FIG. 4 and indicate that while the Si device returned to its original Voc value in under 25 minutes, the CdTe device did not return to its original Voc value within that time frame.

EXAMPLE II

Pd/CdTe devices according to the first embodiment and Pd/PC/CdTe devices according to the second embodiment (with the phthalocyanine being free or substituted with iron or zinc) were formulated. The palladium Schottky layer was 100 angstroms in thickness, and the phthalocyanine layer was 200 angstroms in thickness, except where otherwise noted.

The devices were subjected to very dim room light and exposed to dry air until a steady state Voc value was obtained for dry air. The devices were then subjected to various types of gas: liquid petroleum gas (L.P.G.), dilute hydrogen (1.9% hydrogen, balance argon), ammonia ($NH_3$) and dilute carbon monoxide (3.5% CO, balance dry air). The percentage decrease in the steady state Voc upon exposure to the gas was recorded in the Table as a function of the time of exposure to the gas.

It will be appreciated that generally the variations in open circuit voltage varied not only with the types of gas sorbed, but also the amount of gas sorbed (that is, the exposure time to the gas) up to a saturation point.

To summarize, the present invention provides in one embodiment a self-powered gas detecting device which requires neither an internal electrical storage system nor connection to an external power supply, but rather, upon exposure to light, generates its own photovoltage or photocurrent with the photovoltage or photocurrent changing as a function of the ambient gas composition. The devices can discriminate between particular gases and are inexpensive to construct and maintain and easy and economical to operate. Additionally, the present invention provides embodiments which do not generate their own photovoltage or photocurrent and require either an internal electrical storage system or a connection to an external power supply.

Now that the preferred embodiments of the present invention have been shown and described in detail, various modifications and improvements thereon will become readily apparent to those skilled in the art. Accordingly, the appended claims are to be construed broadly in a manner consistent with the spirit and scope of the invention herein.

TABLE I

DEVICE SENSITIVITIES TO LIQUID PETROLEUM GAS (L.P.G.) DILUTE HYDROGEN (1.9% $H_2$, balance argon) AMMONIA ($NH_3$) AND DILUTE CARBON MONOXIDE (3.5% CO, Balance Dry Air At 60° C.)

| | % Voc Decrease Upon Exposure to Gas as a Function of Time Exposed | | | |
|---|---|---|---|---|
| | Pd/PC/CdTe PC Type | | | Pd/CdTe Without PC |
| | Fe | $H_2$ | Zn | |
| Steady State Dry Air (Voc Values, mv) Gas = L.P.G. | 348 | 249 | 223 | 213 |
| 3 Min. | — | 2.4 | — | 6.1 |
| 9 Min. | 1.4 | 7.2 | — | 38.5 |
| 16 Min. | 8.9 | 18.9 | 4.0 | 65.7 |
| Gas = Dilute Hydrogen | | | | |
| 1 Min. | 16.7 | 26.9 | 21.5 | 81.7 |
| 2 Min. | 21.3 | 45.8 | 39.0 | 87.3 |
| 3 Min. | 29.9 | 56.6 | 47.5 | 88.7 |
| 4 Min. | 33.0 | 60.6 | 52.5 | 89.7 |
| Steady State Dry Air (Voc Values, mv)* Gas = $NH_3$* | 105 | 155 | 132 | — |
| 1 Min. | 80 | 72 | 80 | — |
| Gas = Dilute Carbon Monoxide* | | | | |
| 20 Min. | 1% | +5%** | +23%** | 0% |

*Using another set of devices containing thicker PC layers (1,500 angstroms) relative to the standard thickness of 200 angstroms used.
**These figures represent increases in Voc above the dry air value.

We claim:

1. A gas sensing device comprising a photovoltaic cell which, upon exposure to light, develops a photovoltage or photocurrent which varies as a function of the type of gas sorbed, included in order:
   (i) a conductor,
   (ii) an N-type light-absorbing semiconductor,
   (iii) a light-transmitting gas-absorbing insulating layer of a dielectric having an electrical property which varies with the type of gas sorbed therein, said dielectric being selected from the group consisting of phthalocyanine and clathrating agents; and
   (iv) a light-transmitting gas-penetrable metal Schottky layer.

2. The device of claim 1 wherein said dielectric is phthalocyanine.

3. The device of claim 2 wherein said phthalocyanine is metal-substituted.

4. The device of claim 3 wherein said metal substitution is iron or zinc.

5. The device of claim 1 wherein said metal Schottky layer is non-$H_2$-absorbent.

6. The device of claim 5 wherein said metal Schottky layer is gold.

7. The device of claim 1 wherein said electrical property is photo current.

8. The device of claim 1 wherein said N-type light-absorbing semiconductor is CdTe of Si.

9. The device of claim 1 wherein said N-type light absorbing semiconductor is selected from the group consisting of Si, $CuInSe_2$, CdSe, $Cd_{(1-x)}Hg_xTe$, and GaAs.

10. The device of claim 1 wherein said electrical property also varies with the quantity of the gas sorbed up to a saturation point.

11. The device of claim 1 wherein said electrical property is selected from the group consisting of capacitance, resistance and the cell parameters of open circuit voltage and short circuit current.

12. The device of claim 1 wherein said dielectric is a clathrating agent.

13. The device of claim 12 wherein said clathrating agent is thiourea.

14. The device of claim 12 wherein said clathrating agent is a solid and the guest compound is a gas.

15. The device of claim 1 wherein said metal Schottky layer is composed of a metal selected from the group consisting of palladium and nickel.

16. The device of claim 1 wherein said metal Schottky layer is also gas-absorbing and has an electrical property which varies with the type of gas sorbed therein.

17. A gas sensing device comprising a photovoltaic cell which, upon exposure to light, develops a photovoltage or photocurrent which varies as a function of the type of gas sorbed, included in order:
   (i) a conductor,
   (ii) an N-type light-absorbing semiconductor,
   (iii) a light-transmitting gas-absorbing insulating layer of a dielectric having an electrical property which varies with the type of gas sorbed therein, said dielectric being selected from the group consisting of phthalocyanine and clathrating agents; and
   (iv) a thin P-type light-transmitting, gas-penetrable semiconductor.

18. The device of claim 17 wherein said dielectric is phthalocyanine.

19. The device of claim 18 wherein said phthalocyanine is metal substituted.

20. The device of claim 19 wherein said metal substitution is iron or zinc.

21. The device of claim 17 wherein said dielectric is a clathrating agent.

22. The device of claim 21 wherein said clathrating agent is thiourea.

23. The device of claim 21 wherein said clathrating agent is a solid and the guest compound is a gas.

24. The device of claim 17 wherein said electrical property is photocurrent.

25. The device of claim 17 wherein said N-type light-absorbing semiconductor is CdTe or Si.

26. The device of claim 17 wherein said N-type light-absorbing semiconductor is selected from the group consisting of Si, CuInSe$_2$, CdSe, Cd$_{(1-x)}$Hg$_x$Te, and GaAs.

27. The device of claim 17 wherein said electrical property also varies with the quantity of the gas sorbed up to a saturation point.

28. The device of claim 17 wherein said electrical property is selected from the group consisting of capacitance, resistance and the cell parameters of open circuit voltage and short circuit current.

29. The device of claim 17 wherein said P-type semiconductor is also gas-absorbing and has an electrical property which varies with the type of gas sorbed therein.

30. A method of sensing gas comprising the steps of:
   (A) providing a photovoltaic cell which, upon exposure to light, develops a photovoltage or photocurrent which varies as a function of the type of gas sorbed, including in order, a conductor, an N-type light-absorbing semiconductor, and a light-transmitting gas-absorbing metal Schottky layer having an electrical property which varies with the type of gas absorbed therein;
   (B) exposing the gas-absorbing metal Schottky layer to the gas and the N-type light-absorbing semiconductor to the light; and
   (C) correlating the photovoltage or photocurrent as a function of the type of gas sorbed by the metal Schottky layer.

31. The method of claim 30, wherein the metal Schottky layer is composed of a metal selected from the group consisting of palladium and nickel.

32. The method of claim 30 wherein the N-type light-absorbing semiconductor is CdTe or Si.

33. The method of claim 30 wherein the N-type light-absorbing semiconductor is selected from the group consisting of Si, CuInSe$_2$, CdSe, Cd$_{(1-x)}$Hg$_x$Te, and GaAs.

34. The method of claim 30 wherein the electrical property also varies with the quantity of the gas sorbed up to a saturation point.

35. The method of claim 30 wherein the electrical property is selected from the group consisting of capacitance, resistance and the cell parameters of open circuit voltage and short circuit current.

36. A method of sensing gas comprising the steps of:
   (A) providing a photovoltaic cell which, upon exposure to light, develops a photovoltage or photocurrent which varies as a function of the type of gas sorbed, including in order, a conductor, an N-type light-absorbing semiconductor, a light-transmitting gas-absorbing insulating layer of a dielectric having an electrical property which varies with the type of gas sorbed therein, and a light-transmitting gas-penetrable metal Schottky layer;
   (B) exposing the metal Schottky layer to the gas and to light; and
   (C) correlating the photovoltage or photocurrent as a function of the type of gas sorbed by the dielectric.

37. The method of claim 36 wherein the dielectric is phthalocyanine.

38. The method of claim 37 wherein the phthalocyanine is metal substituted.

39. The method of claim 38 wherein the metal substitution is iron or zinc.

40. The method of claim 36 wherein the dielectric is a clathrating agent.

41. The method of claim 40 wherein the clathrating agent is thiourea.

42. The method of claim 40 wherein the clathrating agent is a solid and the guest compound is a gas.

43. The method of claim 36 wherein the electrical property is photocurrent.

44. The method of claim 36 wherein the N-type light-absorbing semiconductor is CdTe or Si.

45. The method of claim 36 wherein the N-type light-absorbing semiconductor is selected from the group consisting of Si, CuInSe$_2$, CdSe, Cd$_{(1-x)}$Hg$_x$Te, and GaAs.

46. The method of claim 36 wherein the electrical property also varies with the quantity of the gas sorbed up to a saturation point.

47. The method of claim 36 wherein the electrical property is selected from the group consisting of capacitance, resistance and the cell parameters of open circuit voltage and short circuit current.

48. The method of claim 36 wherein the metal Schottky layer is non-H$_2$-absorbent.

49. The method of claim 36 wherein the metal Schottky layer is gold.

50. The method of claim 36, wherein the metal Schottky layer is composed of a metal selected from the group consisting of palladium and nickel.

51. The method of claim 36 wherein the metal Schottky layer is also gas-absorbing and has an electrical property which varies with the type of gas sorbed therein.

52. A method of sensing gas comprising the steps of:
   (A) providing a photovoltaic cell which, upon exposure to light, develops a photovoltage or photocurrent which varies as a function of the type of gas sorbed, including in order, a conductor, an N-type light-absorbing semiconductor, a light-transmitting gas-absorbing insulating layer of a dielectric having an electrical property which varies with the type of gas sorbed therein, and a thin P-type light-transmitting gas-penetrable semiconductor;
   (B) exposing the semiconductor to the gas and to light; and
   (C) correlating the photovoltage or photocurrent as a function of the type of gas sorbed by the semiconductor.

53. The method of claim 52 wherein the dielectric is phthalocyanine.

54. The methodd of claim 53 wherein the phthalocyanine is metal substituted.

55. The method of claim 54 wherein the metal substitution is iron or zinc.

56. The method of claim 52 wherein the dielectric is a clathrating agent.

57. The method of claim 56 wherein the clathrating agent is thiourea.

58. The method of claim 56 wherein the clathrating agent is a solid and the guest compound is a gas.

59. The method of claim 52 wherein the electrical property is photocurrent.

60. The method of claim 52 wherein the N-type light-absorbing semiconductor is CdTe or Si.

61. The method of claim 52 wherein the N-type light-absorbing semiconductor is selected from the group consisting of Si, CuInSe$_2$, CdSe, Cd$_{(1-x)}$Hg$_x$Te, and GaAs.

62. The method of claim 52 wherein the electrical property also varies with the quantity of the gas sorbed up to a saturation point.

63. The method of claim 52 wherein the electrical property is selected from the group consisting of capacitance, resistance and the cell parameters of open circuit voltage and short circuit current.

64. The method of claim 52 wherein the p-type semiconductor is also gas-absorbing and has an electrical property which varies with the type of gas sorbed therein.

* * * * *